(12) United States Patent
Wandler et al.

(10) Patent No.: US 8,426,734 B2
(45) Date of Patent: Apr. 23, 2013

(54) LOW NOISE ECG CABLE AND ELECTRICAL ASSEMBLY

(75) Inventors: David Wandler, Necedah, WI (US); Kirk Mikkelsen, Chaska, MN (US)

(73) Assignee: AMETEK, Inc., Arlington, MN (US)

( * ) Notice: Subject to any disclaimer, the term of this patent is extended or adjusted under 35 U.S.C. 154(b) by 273 days.

(21) Appl. No.: 12/825,196

(22) Filed: Jun. 28, 2010

(65) Prior Publication Data

US 2011/0315426 A1 Dec. 29, 2011

(51) Int. Cl.
*H01B 7/00* (2006.01)

(52) U.S. Cl.
USPC .................. 174/113 R; 174/102 SC

(58) Field of Classification Search .............. 174/113 R, 174/102 SC, 120 SC
See application file for complete search history.

(56) References Cited

U.S. PATENT DOCUMENTS

| | | | | |
|---|---|---|---|---|
| 3,660,592 A | * | 5/1972 | Anderson | 174/114 R |
| 4,143,238 A | * | 3/1979 | Sheth | 174/107 |
| 4,317,000 A | * | 2/1982 | Ferer | 174/70 R |
| 4,486,721 A | * | 12/1984 | Cornelius et al. | 333/1 |
| 4,707,569 A | * | 11/1987 | Yoshimura et al. | 174/116 |
| 5,250,755 A | * | 10/1993 | Dinzen et al. | 174/102 SC |
| 5,397,855 A | | 3/1995 | Ferlier | |
| 6,218,624 B1 | | 4/2001 | Hanssen et al. | |
| 6,225,565 B1 | * | 5/2001 | Prysner | 174/120 SC |
| 6,870,109 B1 | | 3/2005 | Villarreal | |
| 6,930,242 B1 | * | 8/2005 | Helfer et al. | 174/36 |
| 6,982,378 B2 | * | 1/2006 | Dickson | 174/36 |
| 7,481,952 B2 | | 1/2009 | Ren et al. | |
| 2003/0212312 A1 | | 11/2003 | Coffin | |
| 2008/0249390 A1 | | 10/2008 | McIntire | |
| 2008/0255435 A1 | | 10/2008 | Al-Ali | |

* cited by examiner

*Primary Examiner* — Chau Nguyen
(74) *Attorney, Agent, or Firm* — Timothy E Siegel Patent Law, PLLC; Timothy E. Siegel

(57) ABSTRACT

An electrocardiography (ECG) electrical cable, that includes a plurality of insulated conductors, a conductive shield surrounding the plurality of insulated conductors and an insulating jacket surrounding the plurality of insulated conductors and the conductive shield. Also, each of the plurality of insulated conductors includes a low noise coating and the insulated conductors are tightly bound together by a semi-conductive wall interposed between the insulated conductors and the shield, thereby reducing rubbing, which can produce triboelectric effects.

12 Claims, 4 Drawing Sheets

LOW NOISE ECG CABLE AND ELECTRICAL ASSEMBLY

BACKGROUND

Electrocardiography (ECG) is the practice of detecting the electrical activity of the human heart through electrodes. These electrodes are attached to the skin, and their signals are relayed to an ECG machine through leads that are bound into a trunk cable. The leads are made of a conductor, generally tinned copper, surrounded by an insulator, which may be polypropylene. These are then collected together into a trunk that is then provided with a shield, generally made of helically wrapped or woven tinned copper, and a surrounding insulating jacket, which can be polyurethane. So that the cable can be flexible, and to avoid any contact damage between shield and leads, the leads are typically held loosely.

The signal received by the electrodes is very faint, typically in the millivolt range, so it is critically important to minimize noise. The shield prevents outside electromagnetic interference, but internal triboelectric noise remains a problem. There is often movement in the cable due to the patient's breathing, and with the existing design, it is difficult to minimize the buildup of triboelectric charge caused by the rubbing of the loosely bound leads. If this charge builds to a level above the arc point, it will discharge rapidly and create an induced electrical signal that will appear as interfering noise in the conductors.

The shield is helpful in this design because it allows the triboelectric charge caused by the insulated wires rubbing together to be bled away. It is desirable to tightly bind the wires to restrict their movement and reduce triboelectric noise, but a tight polymer wrap would block any triboelectric charges created from reaching the shield, where they could be bled away. This could worsen the effects of triboelectric noise.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an electrocardiography (ECG) electrical cable, that includes a plurality of insulated conductors, a conductive shield surrounding the plurality of insulated conductors and an insulating jacket surrounding the plurality of insulated conductors and the conductive shield. Also, each of the plurality of insulated conductors includes a low noise coating and the insulated conductors are tightly bound together by a semi-conductive wall interposed between the insulated conductors and the shield, thereby reducing rubbing, which can produce triboelectric effects, and preventing damage to the low noise coating and conductor insulation.

In a second separate aspect, the present invention may take the form of a medical electrical cable assembly that includes a plurality of insulated conductors and a conductive shield surrounding the plurality of insulated conductors. Also, each of the plurality of insulated conductors includes a low noise coating and the insulated conductors are tightly bound together by a semi-conductive wall interposed between the insulated conductors and the shield, thereby reducing rubbing, which can produce triboelectric effects, and preventing damage to the low noise coating and conductor insulation.

In a third separate aspect, the present invention may take the form of an electrocardiography (ECG) assembly, having a plurality of electrodes, each electrode electrically connected to an insulated electrical conductor. The insulated conductors are gathered together proximal to the electrodes to form a trunk cable and a conductive shield surrounds the trunk cable portion of the plurality of insulated conductors. Also, an insulating jacket surrounds the trunk cable portion of the plurality of insulated conductors and the conductive shield. Finally, each of the trunk cable portions of the plurality of insulated conductors further includes a low-noise exterior coating and the trunk cable portions are collectively tightly bound together by a semi-conductive low-friction wall interposed between the insulated conductors and the shield, thereby reducing rubbing, which can produce triboelectric effects, and preventing damage to the low noise coating and conductor insulation.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
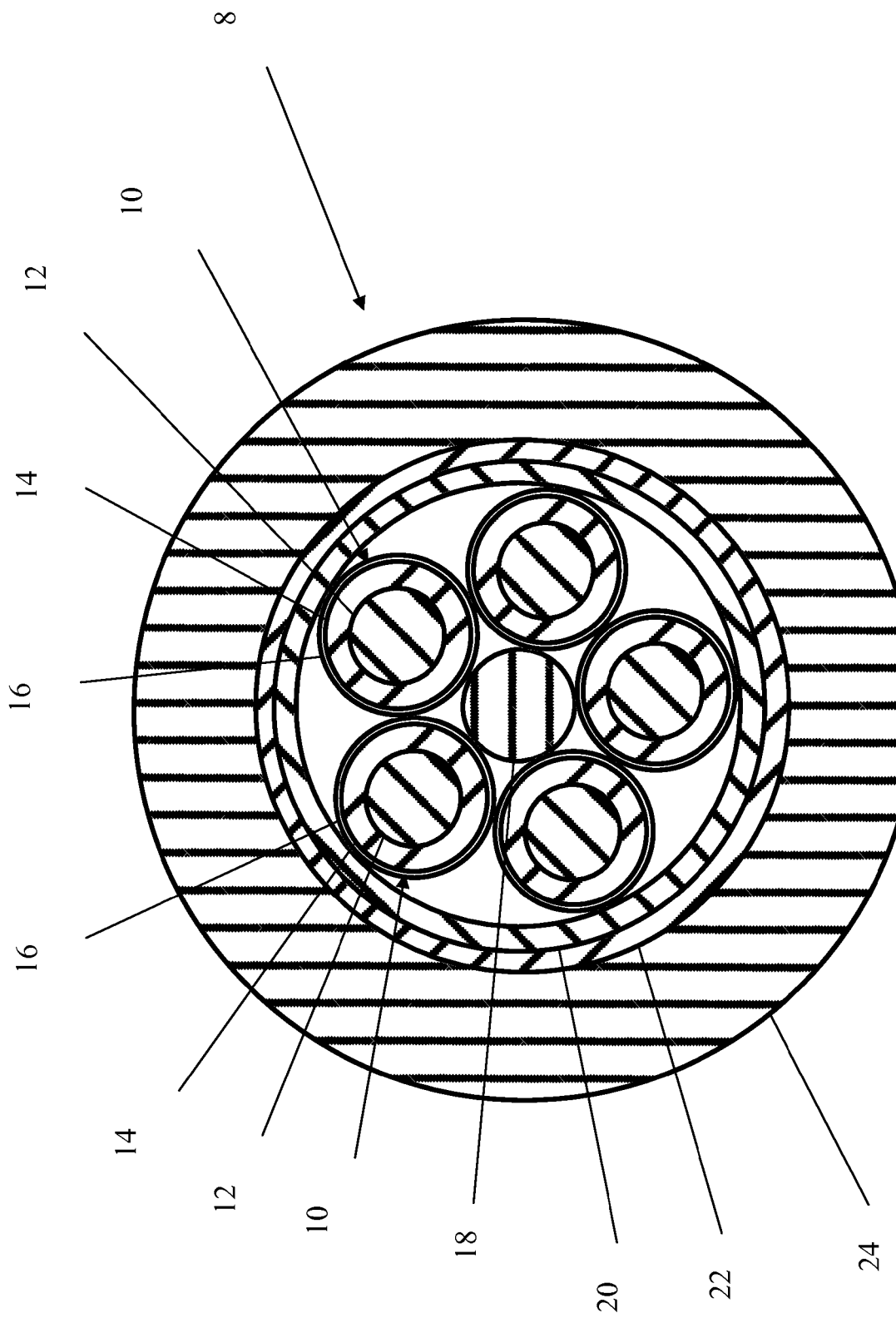
FIG. 1 is a cross-sectional view of a preferred embodiment of a five conductor ECG cable according to the present invention.
Figure 2:
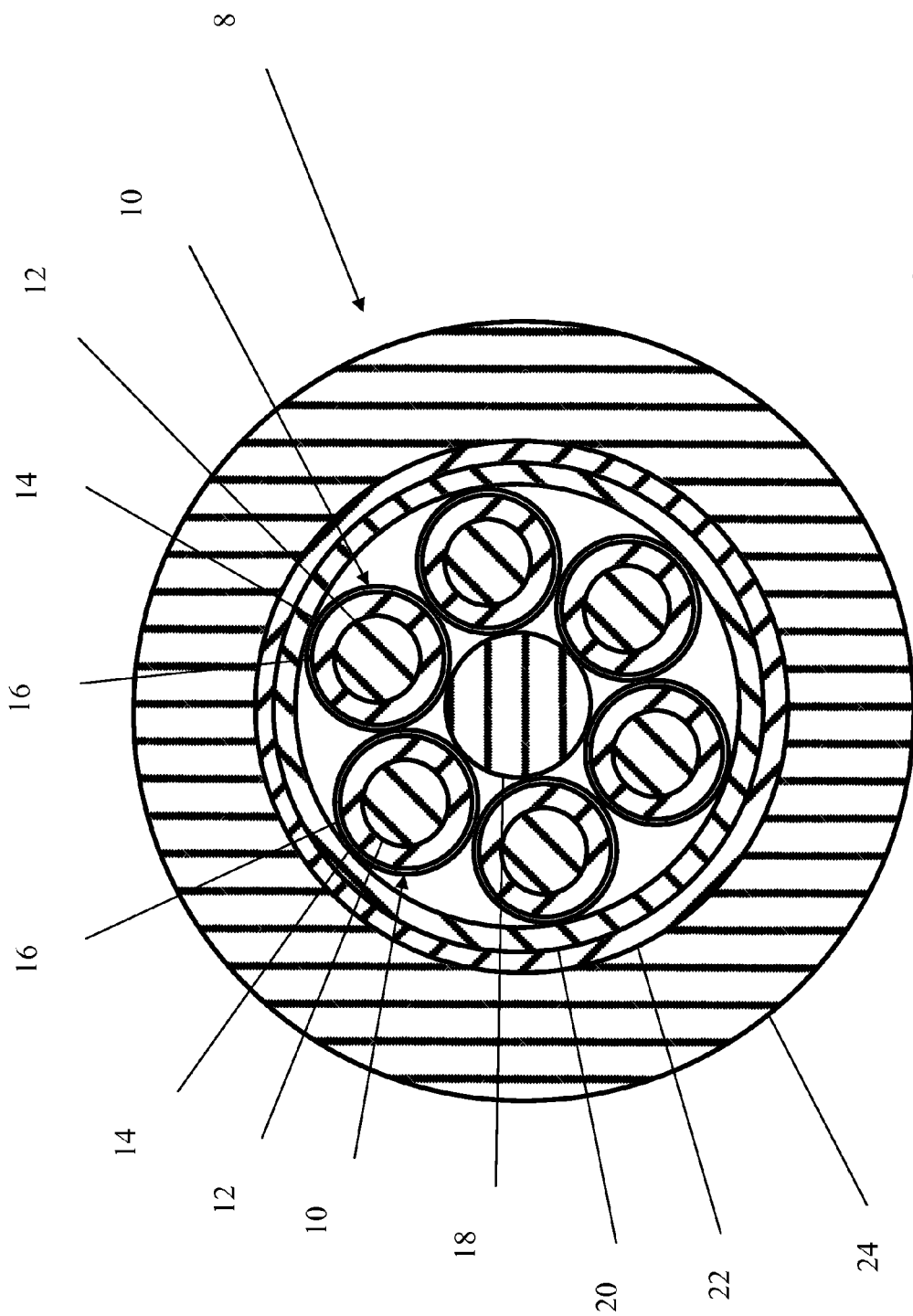
FIG. 2 is a cross-sectional view of a six conductor ECG cable according to the present invention.
Figure 3:
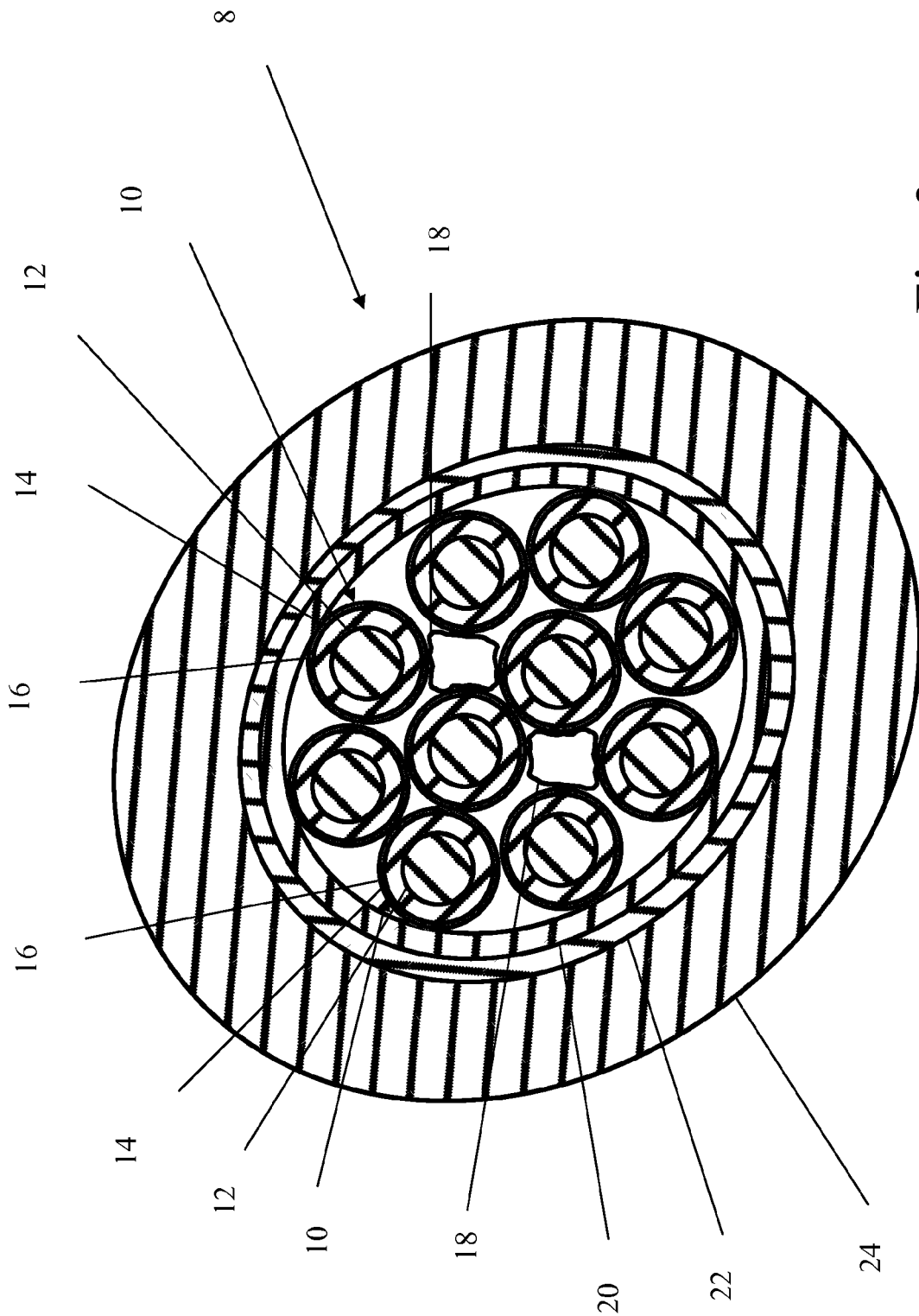
FIG. 3 is a cross-sectional view of a ten conductor ECG cable according to the present invention.

In one preferred embodiment the present invention takes the form of an ECG trunk cable 8 with a set of leads 10 wrapped together around a central circular filler 18. Referring to FIG. 1, the leads 10 are composed of a copper conductor 12, which is surrounded by a polypropylene insulator 14. This is, in turn, coated by a low noise coating wall 16. Leads 10 are bound tightly together by semi-conductive wrapping 20, made of semi-conductive PTFE tape. This is surrounded by a conductive shield 22 of braided tinned copper. The entire cable is then surrounded by insulating jacket 24 of polyurethane. Referring to FIG. 2, the filler 18 can be made larger to accommodate more than five leads 10 or smaller to accommodate fewer leads; common lead counts are three, five, six, or ten. FIG. 3 shows a 10 lead cable, in which two fillers 18 are used and which has a slightly ellipsoid cross-sectional shape. Fillers are used to make the cable is round in cross-section as is practical, given the lead count. The leads 10 and filler(s) 18 are assembled using a braiding machine, which will be familiar to skilled persons.

The tinned copper conductor for the leads is 26 gauge wire. The low noise semi-conductive wall 16 needs to be semi-conductive and smooth to prevent triboelectric noise caused by the rubbing of insulators. The wall 16 is about 3-5 microns thick. In one preferred embodiment, wall 16 is formed in accordance with the teachings of U.S. Pat. No. 6,218,624, which is hereby incorporated by reference as if fully set forth herein. In the method taught, layer 16 is formed as an electroconductive lacquer layer, from a suspension of silver particles in a thermoplastic synthetic resin, by running an insulated wire through a bath of the suspension. In an alternative preferred embodiment low noise leads 10, having a surface resistivity of 1,000 ohm/square, created by coating insulated leads with a carbon filled solution, may be obtained from Winfox Cable Solutions (http://www.winfox.com.tw/), by specifying the dimensions and the required surface resistivity.

In an alternative preferred embodiment, low noise layer 16 is formed by extrusion. In this embodiment, a mixture of carbon particles in polyethylene, polypropylene or polyvinyl chloride is extruded onto insulating layer 14.

For the purposes of this application any insulated lead having a surface resistivity of less than $10^9$ Ohm/square is a "low noise coating." It is generally desirable, however, for a low noise coating to have a surface resistivity of less than $10^6$ Ohm/square.

The semi-conductive PTFE tape used in the PTFE wall 20 is produced by mixing PTFE with carbon, making the PTFE tape semi-conductive. The wall 20 is 0.003 inches thick. Unlike the tinned copper shield 22, the PTFE tape is smooth and can tightly bind the leads 10 without damaging them. It may be produced in accordance with the method described in U.S. Pat. No. 7,481,952 B2 issued Jan. 27, 2009, which is hereby incorporated by reference as if fully set forth herein. In a preferred embodiment PTFE tape is wrapped with a pitch or lay of ½ overlap per turn, so that wall 20 is as twice as thick as the tape it is made from.

The semi-conductive PTFE wall 20 and low noise wall 16 help to reduce the triboelectric noise present in ECG cables lacking these elements, which is caused by the rubbing of leads due to patient-caused movement. The low noise wall 16 is semi-conductive, reducing and bleeding away triboelectric charge. The smooth semi-conductive PTFE wall 20 is wrapped tightly around the leads 10, providing protection for the delicate conductive walls 16, against shield 22, and providing an additional semi-conductor to bleed away triboelectric charges. Moreover, PTFE wall 20 acts to restrict the movement of leads 8, thus reducing triboelectric noise caused by rubbing but permitting the cable 8 to be flexible by providing a smooth, low-friction slip-layer. The benign low friction qualities of PTFE also avoids damage to walls 16, by PTFE 20 itself.

Figure 4:
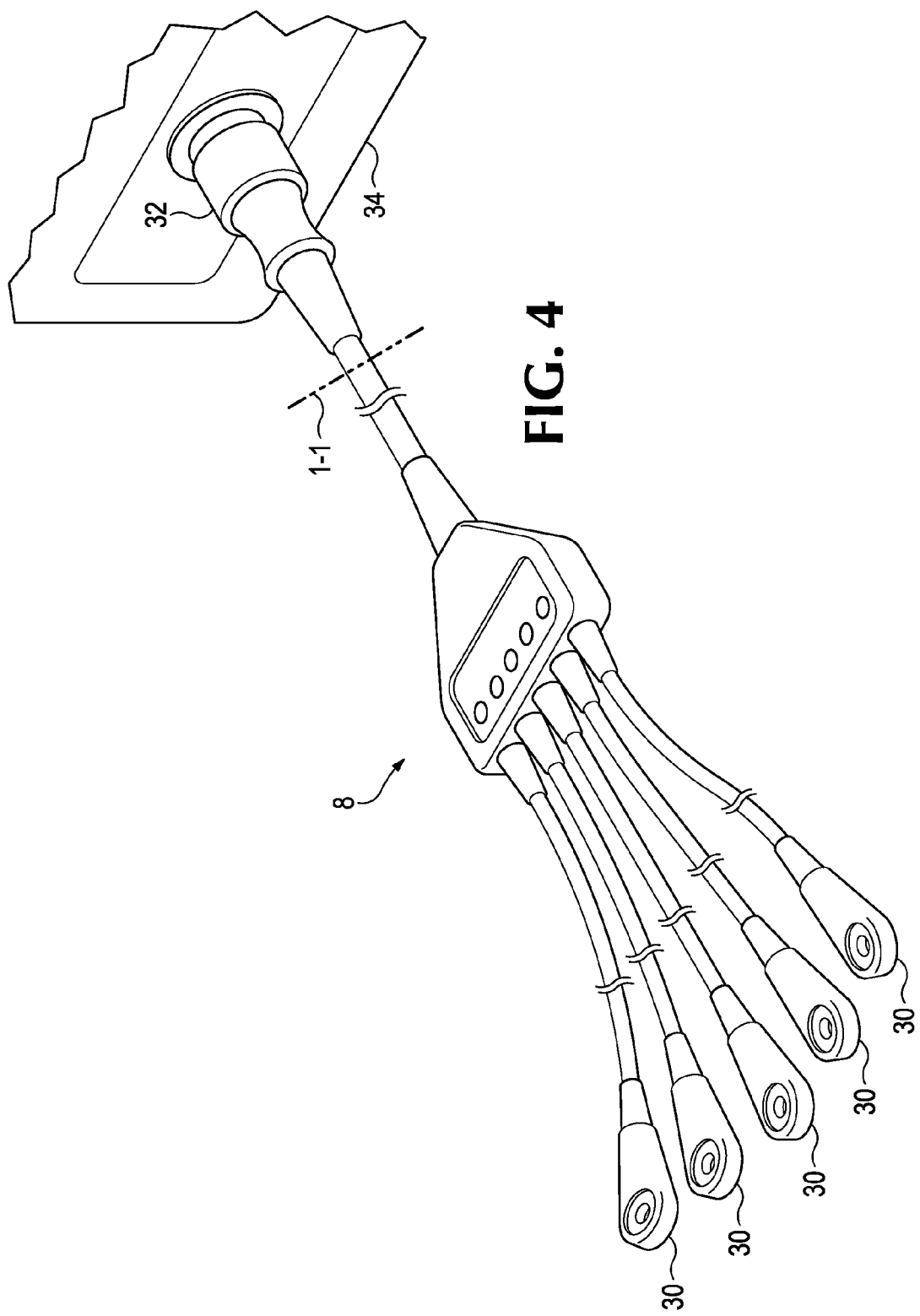
FIG. 4 is an isometric view of a five conductor ECG cable, which may embody the present invention.

Skilled persons will readily recognize that the above described cross-sectional structure of FIG. 1, may be implemented in a 5 lead ECG cable, more fully shown in FIG. 4, with the view of FIG. 1 taken along view line 1-1 and with each conductor 12 electrically connected to a separate electrode 30 and with connector 32 connecting the cable to an ECG machine 34.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An electrocardiography (ECG) electrical cable, comprising:
    (a) a plurality of insulated conductors;
    (b) a conductive shield surrounding said plurality of insulated conductors;
    (c) an insulating jacket surrounding said plurality of insulated conductors and said conductive shield; and
    (d) wherein said each of said plurality of insulated conductors further includes a low-noise exterior coating having a surface resistivity of less than $10^9$ ohms/square and are collectively tightly bound together by a semi-conductive low-friction wall made of PTFE tape wrapped about said plurality of insulated conductors and said wall touching at least some of said insulated conductors and interposed between said insulated conductors and said shield, thereby reducing rubbing, which can produce triboelectric effects.

2. The ECG cable of claim 1, wherein said low-noise exterior coating is a conductive lacquer comprised of silver particles suspended in thermoplastic synthetic resin.

3. The ECG cable of claim 1, wherein said low-noise coating has a surface resistivity of less than $10^6$ Ohms/square.

4. The ECG cable of claim 1, wherein said low-noise coating has a surface resistivity of less than $10^4$ Ohms/square.

5. A medical electrical cable assembly, comprising a structure having:
    (a) a plurality of insulated conductors;
    (b) a conductive shield surrounding said plurality of insulated conductors;
    (c) wherein each of said plurality of insulated conductors further includes a low-noise exterior coating having a surface resistivity of less than $10^9$ ohms/square and are collectively tightly bound together by a semi-conductive, low-friction, wall made of PTFE tape wrapped about said plurality of insulated conductors and said wall touching at least some of said insulated conductors and interposed between said insulated conductors and said shield, thereby reducing rubbing, which can produce triboelectric effects.

6. The medical electrical cable of claim 5, wherein said low-noise coating has a surface resistivity of less than $10^6$ Ohms/square.

7. The medical electrical cable of claim 5, wherein said low-noise coating has a surface resistivity of less than $10^4$ Ohms/square.

8. The medical electrical cable assembly of claim 5, further including an insulating jacket, surrounding said shield.

9. The medical electric cable of claim 5, wherein each said low-noise exterior coating is a conductive lacquer comprised of silver particles suspended in thermoplastic synthetic resin.

10. The medical electric cable of claim 5, further being an ear, nose and throat treatment cable.

11. An electrocardiography (ECG) electrical cable, comprising:
    (a) a plurality of insulated conductors spaced around one or more central fillers;
    (b) a conductive shield surrounding said plurality of insulated conductors;
    (c) an insulating jacket surrounding said plurality of insulated conductors and said conductive shield; and
    wherein said each of said plurality of insulated conductors further includes a low-noise exterior coating having a surface resistivity of less than $10^9$ ohms/square and are collectively tightly bound together by a semi-conductive low-friction wall touching at least some of said insulated conductors and interposed between said insulated conductors and said shield, thereby reducing rubbing, which can produce triboelectric effects.

12. The ECG cable of claim 11, wherein said fillers are composed of nylon fibers.

* * * * *